(12) United States Patent
Reddy et al.

(10) Patent No.: US 12,168,122 B2
(45) Date of Patent: *Dec. 17, 2024

(54) SUBSTERNAL PLACEMENT OF A PACING AND/OR DEFIBRILLATING ELECTRODE

(71) Applicant: CAMERON HEALTH, INC., St. Paul, MN (US)

(72) Inventors: G. Shantanu Reddy, Minneapolis, MN (US); Bruce A. Tockman, Scandia, MN (US)

(73) Assignee: CAMERON HEALTH, INC., St. Paul, MN (US)

( * ) Notice: Subject to any disclaimer, the term of this patent is extended or adjusted under 35 U.S.C. 154(b) by 681 days.

This patent is subject to a terminal disclaimer.

(21) Appl. No.: 17/405,224

(22) Filed: Aug. 18, 2021

(65) Prior Publication Data

US 2021/0379364 A1  Dec. 9, 2021

Related U.S. Application Data

(63) Continuation of application No. 15/208,682, filed on Jul. 13, 2016, now Pat. No. 11,123,547.

(Continued)

(51) Int. Cl.
*A61N 1/05* (2006.01)
*A61B 17/04* (2006.01)
(Continued)

(52) U.S. Cl.
CPC ........ *A61N 1/0504* (2013.01); *A61B 17/0401* (2013.01); *A61B 90/361* (2016.02);
(Continued)

(58) Field of Classification Search
CPC .. A61N 1/05–0597; A61N 1/39; A61N 1/362; A61B 17/0401; A61B 17/3468
See application file for complete search history.

(56) References Cited

U.S. PATENT DOCUMENTS

| 4,887,606 A | 12/1989 | Yock et al. |
| 6,647,292 B1 | 11/2003 | Bardy et al. |

(Continued)

FOREIGN PATENT DOCUMENTS

| JP | 2004508906 A | 3/2004 |
| JP | 2005507747 A | 3/2005 |

(Continued)

OTHER PUBLICATIONS

"Medtronic 6996SQ Subcutaneous, unipolar lead with defibrillation coil electrode", Technical Manual, Medtronic, Inc., M948140A001C, May 10, 2012, 22 pgs.

(Continued)

*Primary Examiner* — Ariana Zimbouski
*Assistant Examiner* — Mikail A Mannan
(74) *Attorney, Agent, or Firm* — Seager, Tufte & Wickhem LLP

(57) ABSTRACT

New methods for implanting a cardiac therapy system include implanting a lead of the system substernally anterior of the heart without attaching to the myocardium or pericardium. An illustration includes placement of an anchor beneath the sternum in the vicinity of one of the sternal angle, a location superior of the ventricles, the area bounded by the 2nd or 3rd ribs, and level with the aortic arch. A tension element or tether is attached to the anchor and a lead is introduced over the tension element or tether and secured in a desired position relative to the anchor. Other examples also include implantation, substernally, of a lead without the use of a pre-tunneling tool or sheath over the lead itself, for example by using an advancing tool for pushing the lead into position.

15 Claims, 19 Drawing Sheets

Related U.S. Application Data

(60) Provisional application No. 62/195,695, filed on Jul. 22, 2015.

(51) Int. Cl.
| | | |
|---|---|---|
| *A61B 17/32* | (2006.01) | |
| *A61B 17/34* | (2006.01) | |
| *A61B 90/00* | (2016.01) | |
| *A61N 1/362* | (2006.01) | |

(52) U.S. Cl.
CPC ............. *A61N 1/05* (2013.01); *A61N 1/3629* (2017.08); *A61B 2017/0417* (2013.01); *A61B 2017/320056* (2013.01); *A61B 17/3468* (2013.01); *A61N 1/059* (2013.01)

(56) References Cited

U.S. PATENT DOCUMENTS

| | | |
|---|---|---|
| 6,721,597 B1 | 4/2004 | Bardy et al. |
| 8,868,214 B2 | 10/2014 | Osypka |
| 2004/0102804 A1 | 5/2004 | Chin |
| 2004/0210245 A1 | 10/2004 | Erickson et al. |
| 2005/0246006 A1 | 11/2005 | Daniels |
| 2012/0029335 A1 | 2/2012 | Sudam et al. |
| 2012/0191090 A1 | 7/2012 | Sugahara et al. |
| 2014/0330287 A1 | 11/2014 | Thompson-Nauman et al. |
| 2014/0330327 A1 | 11/2014 | Thompson-Nauman et al. |
| 2014/0330328 A1 | 11/2014 | Christie et al. |
| 2014/0330329 A1 | 11/2014 | Thompson-Nauman et al. |
| 2015/0105793 A1 | 4/2015 | Cole |
| 2015/0209077 A1 | 7/2015 | Marshall |
| 2015/0343228 A1 | 12/2015 | Strommer et al. |
| 2016/0144192 A1 | 5/2016 | Sanghera et al. |

FOREIGN PATENT DOCUMENTS

| | | |
|---|---|---|
| WO | 2004073506 A2 | 9/2004 |
| WO | 2014081978 A1 | 5/2014 |

OTHER PUBLICATIONS

"Medtronic 6996T Tunneling tool", Technical Manual, Medtronic, Inc., M971381A001, Jul. 28, 2017, 10 pgs.

Invitation to Pay Additional Fees And, Where Applicable, Protest Fee, PCT/US2016/043128, mailed Nov. 4, 2016.

Geunther et al., "Substernal lead implantation: a novel option to manage DFT failure in S-ICD patients," Clin Res Cardiol., vol. 104, pp. 189-191, 2015.

Boersma et al; "Therapy from a Novel Substernal Lead", The ASD2 Study, JACC Clinical Elecrophysiology, vol. 5, No. 2, pp. 186-196, Feb. 2019.

Crozier et al; "First-in-Human Chronic Implant Experience of the Substernal Extravascular Implantable Cardioverter-Defribrillator," JACC: Clinical Electrophysiology, vol. 6, No. 12, pp. 1525-1536, 2020.

Swerdlow et al; "Design and Preliminary Results of Sensing and Detection for an Extravascular Implantable Cardioverter-Defibrillator," JACC Clinical Electrophysiology, 13 pages, 2021.

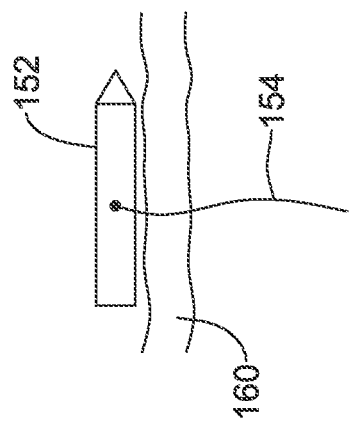
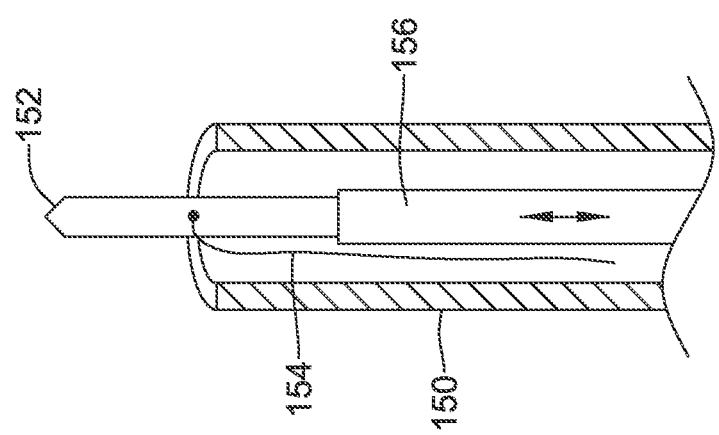
FIG. 4B
FIG. 4A

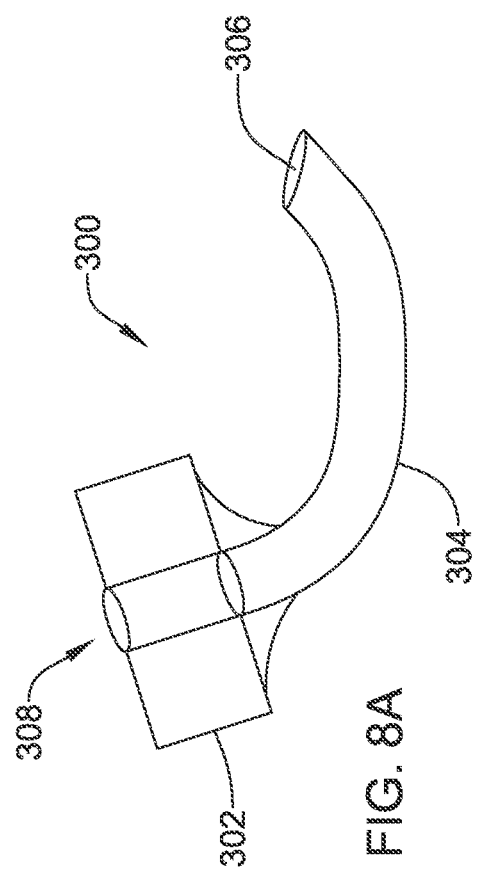
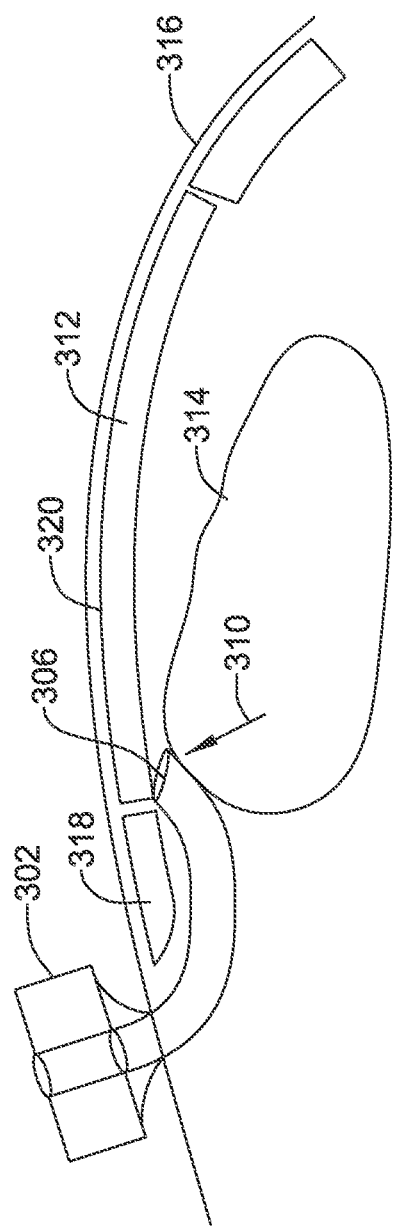

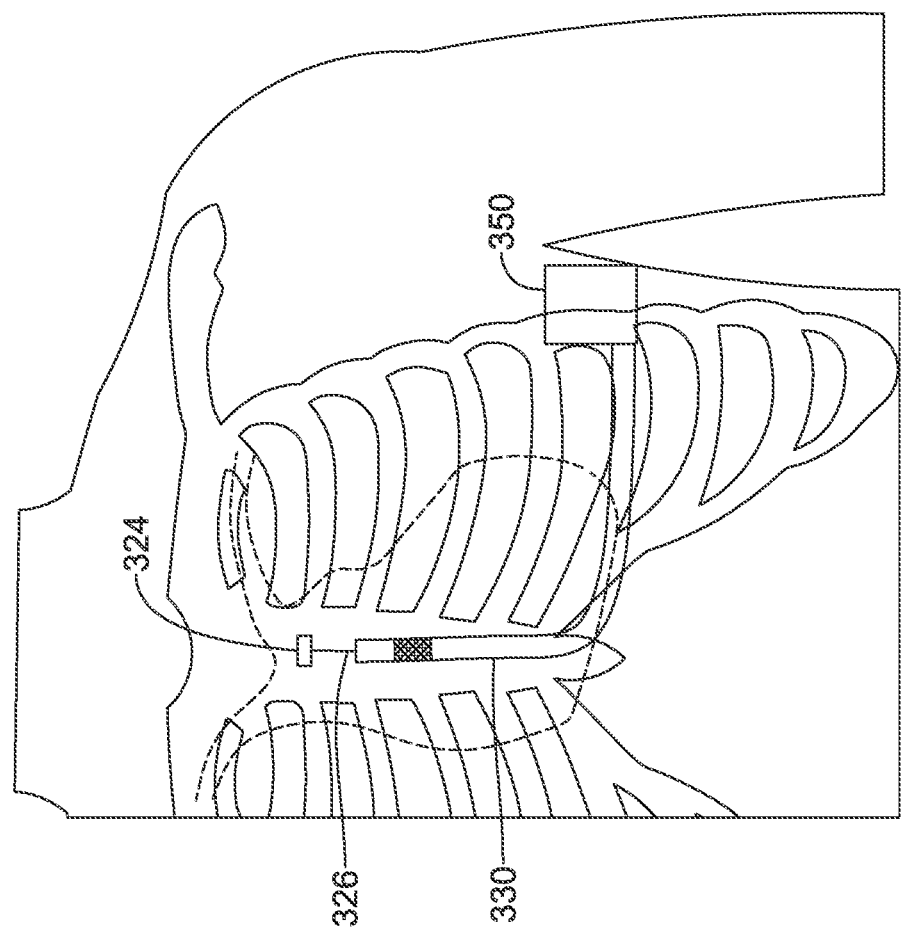

SUBSTERNAL PLACEMENT OF A PACING AND/OR DEFIBRILLATING ELECTRODE

CROSS REFERENCE TO RELATED APPLICATIONS

This application is a continuation of U.S. application Ser. Ser. No. 15/208,682, filed Jul. 13, 2016, which claims the benefit of and priority to U.S. Provisional Application Ser. No. 62/195,695, filed Jul. 22, 2015 and titled SUBSTERNAL PLACEMENT OF A PACING AND/OR DEFIBRILLATING ELECTRODE, the disclosures of which are incorporated herein by reference.

BACKGROUND

Presently available subcutaneous-only defibrillator systems (the S-ICD System™ and Emblem™ S-ICD System™, Boston Scientific Corporation) make use of a subcutaneously placed parasternal lead having sensing electrodes and a defibrillation coil electrode. This parasternal lead is placed over or just to the left of the sternum in most patients, though occasional interest has been shown in a right parasternal location as well. The implantable pulse generator of the system is implanted in the left axilla approximately level with the inframammary crease. Tunneling steps are performed to place the lead subcutaneously in the desired configuration.

The placement of such systems entirely subcutaneously calls for higher pacing thresholds, making the delivery of anti-bradycardia or anti-tachycardia pacing uncomfortable for the patient. Some patients exhibit high defibrillation thresholds at this location as well, and may not be able to receive a subcutaneous-only system, instead being forced to receive a transvenous or other system even if they are anatomically poorly suited to such systems or simply do not want a lead in or on the heart. At least one clinical group has suggested that the lead and therapy electrodes of the subcutaneous-only defibrillator could instead be implanted substernally. (See Guenther et al., Substernal Lead Implantation: A Novel Option to Manage DFT Failure in S-ICD Patients, Clin. Res. Cariol (2015) 104:189-191).

Overview

The present inventors have recognized, among other things, the suggested manner of placing a substernal lead in the Guenther et al. article includes the use of a tunneling tool and sheath, and does not include any anchoring of the distal tip of the electrode. An alternative or enhanced approach is desirable.

A first non-limiting example takes the form of an insertion sheath comprising an external port, and an insertion portion having a curved shaft and a tip, wherein the sheath is sized and shaped such that, when inserted adjacent the xiphoid of a patient, the insertion portion curves around the xiphoid in a direction toward the sternal body of the patient. A second non-limiting example takes the form of an insertion sheath as in the first non-limiting example, wherein the tip is beveled. A third non-limiting example takes the form of an insertion sheath as in either of the first two non-limiting examples, wherein the curved shaft is configured to bias an instrument passed through it toward the sternal body and away from the heart and pericardium when inserted adjacent the xiphoid of the patient.

A fourth non-limiting example takes the form of an anchoring system for placement of a cardiac lead at a location outside of the heart and pericardium, on the back side of the sternum, the system comprising an anchor placement tool including a proximal handle, a junction adapted to receive a tension member, and a distal portion which ends in a distal end; and a tension member having an anchor thereon, wherein the anchor is disposed at the distal end of the anchor placement tool, with the tension member extending proximally therefrom within the anchor placement tool until exiting at the junction.

A fifth non-limiting example takes the form of an anchoring system as in the fourth non-limiting example, wherein the anchor placement tool has a length from the proximal handle to the distal end in the range of about 30 to 60 centimeters. A sixth non-limiting example takes the form of an anchoring system as in either of the fourth or fifth non-limiting examples, in which the distal portion of the anchor placement tool has a length from the junction to the distal end of about 20-30 centimeters. A seventh non-limiting example takes the form of an anchoring system as in any of the fourth to sixth non-limiting examples, in which the distal portion of the anchor placement tool is steerable, and the proximal handle comprises means for steering the distal portion. An eighth non-limiting example takes the form of an anchoring system as in any of the fourth to seventh non-limiting examples, in which the anchor placement tool comprises a push member for pushing the anchor out of the distal end and into a desired tissue.

A ninth non-limiting example takes the form of an anchoring system as in any of the fourth to eighth non-limiting examples, in which the anchor placement tool comprises a plurality of lumens including at least a lumen for a visualization element. A tenth non-limiting example takes the form of an anchoring system as in any of the fourth to eighth non-limiting examples, in which the anchor placement tool is an endoscope. An eleventh non-limiting example takes the form of an anchoring system as in any of the fourth to tenth non-limiting examples, in which the anchor placement tool includes a Doppler sensor near the distal end thereof.

A twelfth non-limiting example takes the form of an anchoring system as in any of the fourth to eleventh non-limiting examples, in which the anchor has an expandable element which is constrained during introduction by the distal portion and/or distal end of the anchor placement tool, and which expands upon release of the anchor beyond the distal end of the anchor placement tool. Thirteenth to fifteenth non-limiting examples takes the form of an anchoring system as in any of the fourth to twelfth non-limiting examples, further comprising an insertion sheath as in any of the first to third non-limiting examples.

A sixteenth non-limiting example takes the form of a method of implanting a medical device including a lead having a distal portion and a proximal end, the method comprising: placing an anchor adjacent the posterior of the sternum with a tension element coupled to the anchor in the thoracic cavity of a patient; advancing a the lead using the tension element to a desired location in the direction of the anchor; securing the distal portion of the lead at or near the anchor; and attaching a proximal end of the lead to a canister at a subcutaneous location on the patient's thorax.

A seventeenth non-limiting example takes the form of a method as in the sixteenth non-limiting example, wherein the step of securing the distal portion of the lead at or near the anchor includes securing the tension element at the proximal end of the lead after the lead is advanced to the desired location. An eighteenth non-limiting example takes the form of a method an in either of the sixteenth or seventeenth non-limiting examples, wherein the step of placing the anchor is performed by inserting a stylet or cannula beneath the sternum from a location near the patient's xiphoid and advancing a distal portion of the stylet or cannula to a desired location for the anchor.

A nineteenth non-limiting example takes the form of a method as in the eighteenth non-limiting example, wherein the desired location is selected from a group of positions consisting of a location approximately at the sternal angle, a location between the second and third ribs, a location approximately level with the thymus, a location even with the aortic arch, and a location even with the stop of the superior vena cava.

A twentieth non-limiting example takes the form of a method as in either of the eighteenth or nineteenth non-limiting examples, further comprising inserting an insertion sheath through an incision near the xiphoid and beneath the sternum, wherein the insertion sheath comprises a proximal end and a distal end with a curve therebetween to bias the distal end toward the backside of the sternum, and passing the cannula through the insertion sheath such that the cannula is biased by the insertion sheath against the backside of the sternum in order to insert the cannula. A twenty-first non-limiting example takes the form of a method as in either of the eighteenth or nineteenth non-limiting examples, wherein the stylet or cannula is a cannula having a lumen and a push member within the lumen for pushing the anchor out of the lumen upon reaching the desired location for the anchor. A twenty-second non-limiting example takes the form of a method as in the twenty-first non-limiting example, wherein the tension element passes through at least a distal portion of the cannula. A twenty-third non-limiting example takes the form of a method as in either of the eighteenth or nineteenth non-limiting examples, wherein the stylet or cannula is a stylet for pushing the anchor to the desired location, and the tension element is pulled along the outside of the stylet by its attachment to the anchor during the step of inserting the stylet beneath the sternum.

A twenty-fourth non-limiting example takes the form of a method as in any of the sixteenth to twenty-third non-limiting example, wherein the anchor is a t-bar. A twenty-fifth non-limiting example takes the form of a method as in any of the sixteenth to twenty-fourth non-limiting examples, wherein the subcutaneous location is near the patient's left axilla and the method further comprises subcutaneously tunneling the proximal end of the lead to the subcutaneous location.

A twenty-sixth non-limiting example takes the form of a method as in any of the sixteenth to twenty-fifth non-limiting examples, wherein the step of placing the anchor adjacent the posterior of the sternum comprises attaching the anchor to connective tissue of the mediastinum. A twenty-seventh non-limiting example takes the form of a method as in the twenty-sixth non-limiting example, wherein the step of attaching the anchor to connective tissue of the mediastinum comprises piercing the connective tissue at approximately the level of the sternal angle. A twenty-eighth non-limiting example takes the form of a method as I the twenty-sixth non-limiting example, wherein the step of attaching the anchor to connective tissue of the mediastinum comprises piercing the connective tissue just inferior to the manubrium. A twenty-ninth non-limiting example takes the form of a method as in the twenty-sixth non-limiting example, wherein the step of attaching the anchor to connective tissue of the mediastinum comprises piercing the connective tissue at approximately a region bounded by the level of the 2nd to 3rd ribs. A thirtieth non-limiting example takes the form of a method as in the twenty-sixth non-limiting example, wherein the step of attaching the anchor to connective tissue of the mediastinum comprises piercing the connective tissue at approximately the level of the aortic arch.

A thirty-first non-limiting example takes the form of a method as in any of the sixteenth to thirtieth non-limiting examples, wherein the step of placing the anchor comprises advancing the anchor along the posterior side of the sternum while using a Doppler probe positioned adjacent the anchor to observe the position of the anchor during said advancing. A thirty-second non-limiting example takes the form of a method as in any of the sixteenth to thirty-first non-limiting examples, further comprising visualizing the position of the anchor using an optical visualization tool to observe blood vessels and/or muscle in the vicinity of the desired location.

A thirty-third non-limiting example takes the form of a method of placing a lead for an implantable cardiac therapy system, the lead comprising an element for receiving an advancing tool and one or more electrodes, the method comprising advancing an insertion tool percutaneously to a position near the xiphoid of the patient along the backside of the sternum, wherein the insertion tool is shaped to preferentially direct a member passed therethrough against the back of the sternum, and pushing the lead into a desired position using the advancing tool, wherein the desired position is along the posterior of the sternum, at least superior to the ventricles of the patient's heart, without first tunneling from the insertion tool to the desired location.

A thirty-fourth non-limiting example takes the form of a method of placing a lead for an implantable cardiac therapy system, the lead comprising one or more electrodes, the method comprising securing an anchor at approximately the sternal angle, with a tension element attached thereto, advancing the lead over the tension element to a desired location near the anchor, securing together the tension element and a proximal portion of the lead to hold the lead at a desired position relative to the anchor. A thirty-fifth non-limiting example takes the form of a method as in the thirty-fourth non-limiting example, wherein the step of securing an anchor at approximately the sternal angle includes making an incision near the xiphoid, inserting and advancing an insertion tool beneath the sternum, with the tension element thereon or therein, to a desired position.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIGS. 4A-4B, 5A-5B and 6 each illustrate various designs usable with the system of FIG. 3;

FIGS. 8A-8B show an insertion sheath or tool and its use in a patient;

FIGS. 15-16 show frontal and side views of an implanted configuration following completion of an illustrative method;

DETAILED DESCRIPTION

Figure 1:
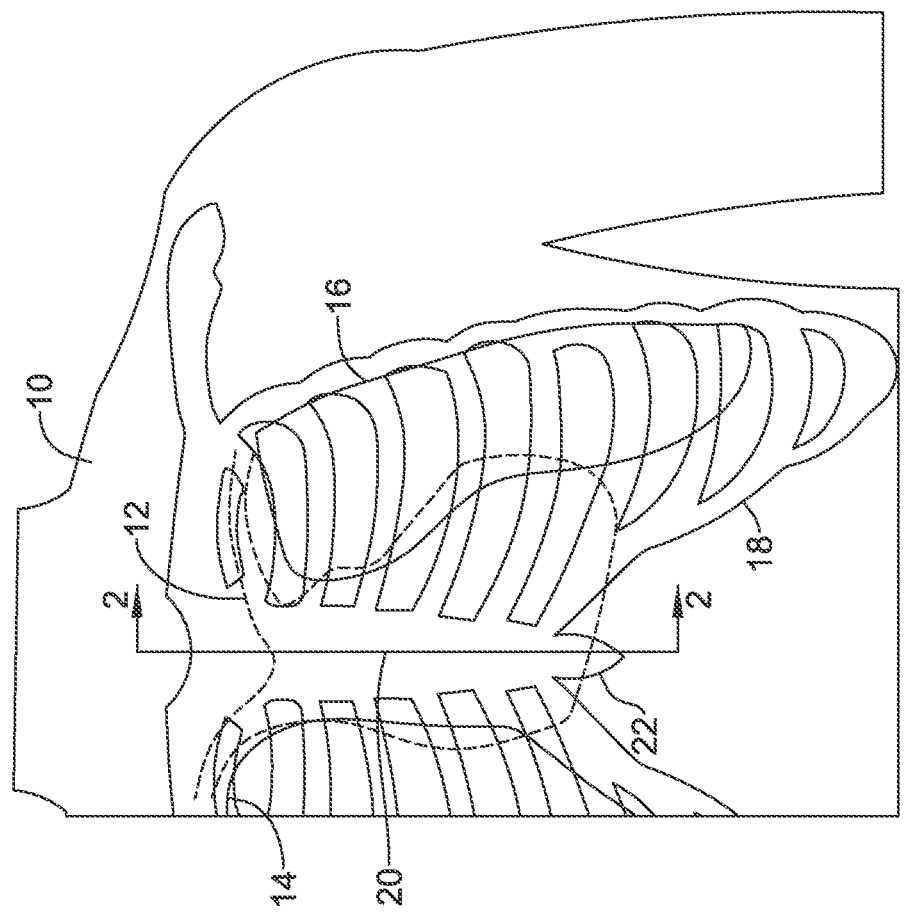
FIGS. 1-2 illustrate certain anatomy of the upper thorax of a patient.
Figure 2:
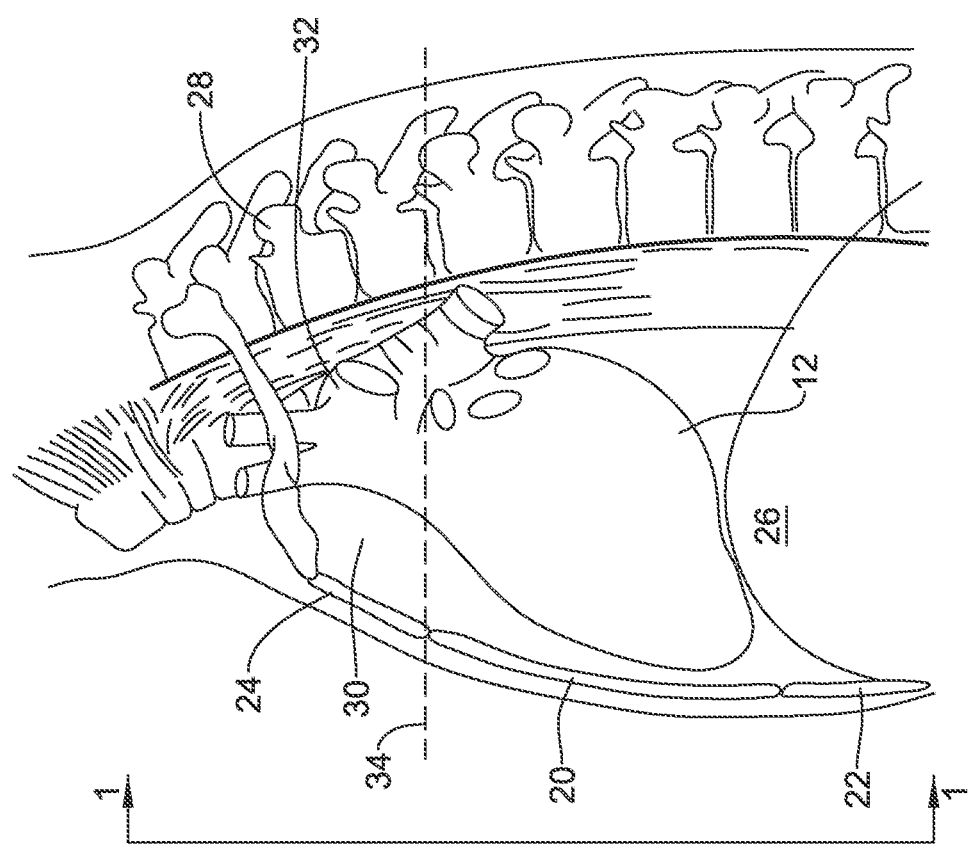

FIGS. 1-2 illustrate certain anatomy of the upper thorax of a patient. As shown in FIG. 1, the patient 10 is shown with the heart 12, the right side of the lung 14, and left side of the lung 16. The sides of the lungs 14/16 generally track the outside of the heart 12, and each of course are protected behind the ribs 18 and sternum 20. The sternum includes the xiphoid process 22.

A section view along line 2-2 from FIG. 1 is shown in FIG. 2. The heart 12 sits in the compartment between the sternum 20 and the vertebrae 28. The sternum 20 actually includes three parts in normal adult anatomy is shown, with the manubrium 24 being superior to the sternal body which terminates inferiorly with the xiphoid process 22. Line 34 illustrates the height of the sternal angle, at the junction of the sternal body and the manubrium 24. For illustrative purposes, the aortic arch is shown at 32 as well. The thymus, which sits approximately in the space 30, superior to the heart 12, is omitted so as to avoid obscuring the Figure to too much detail. The heart 12 sits above the diaphragm 26 as well.

As can be seen from the combined views of FIGS. 1 and 2, the sub-sternal location generally requires inserting a lead between the heart 12 and the sternum 20. The target location in region 30 (FIG. 2) contains some loose connective tissues, muscle, nerves and blood vessels. Anchoring a lead may be desirable, for example, in the region of the sternal angle at the junction of the manubrium 24 and the sternal body, superior to the ventricles (widest lower portion of the heart 12), and/or approximately level with or just inferior to the aortic arch, if the target for therapy is the ventricles of the heart. From such a position, beneath the sternum, the amount of energy required for defibrillation and pacing efficacy would logically be lower than outside of the sternum, since the substernal location is closer to the heart and bone is generally not a very good conductor of electrical energy, at least when speaking in terms of the tissues in the human body. However, tunneling in this region is not so necessary as it may be in other locations, particularly the subcutaneous space, where the innermost layers of dermis must be separated from underlying muscle, connective tissue and fascia. Indeed, the insertion of a tool beneath the sternum is likely to be better understood as requiring positional control—rather than longitudinal force—with a goal of remaining as near as possible to the back of the sternum, to avoid damaging and/or puncturing other anatomical features.

Figure 3:
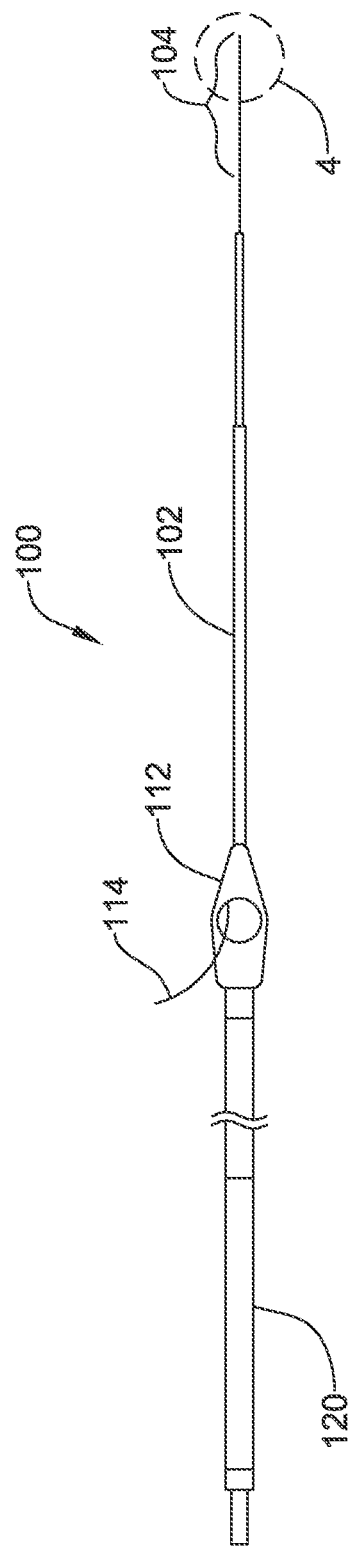
FIG. 3 illustrates an anchoring system that may be used to place a cardiac lead.

FIG. 3 illustrates an anchoring system which may be used in placement of a cardiac lead. The anchor placement tool 100 includes a proximal handle region 120, a junction at 112 through which a tether or tension member 114 exits, and a distal portion 102. The distal portion 102 ends in a distal end 104 for which various embodiments follow. In terms of size, the total length may be in the range of 30-60 centimeters, with the distal portion 102 having a length of about 20-30 centimeters, long enough to reach from the xiphoid to the manubrium in most patients. Other lengths may be used.

If desired, and as further explained below relative to FIGS. 6 and 7A-7B, optical, fluid, and electric or other connectors may also be provided at the handle 120. In some examples, the handle 120 may include a trigger or other mechanism for steering the distal end 104 during advancement beneath the sternum. The overall purpose in some embodiments is to remain close to the back of the sternum until a desired location is reached, and then to secure the anchoring device located at the distal end 104 to the connective tissue in the region of the sternal angle and/or the $2^{nd}$ or $3^{rd}$ rib, and/or superior to the ventricles, and/or inferior to or at the manubrium, and/or approximately level with the thymus, superior vena cava, or aortic arch.

FIGS. 4A-4B, 5A-5B and 6 each illustrate various designs usable with the system of FIG. 3. In FIG. 4A, the anchor placement tool is shown having an outer shaft 150 with a lumen therein in which an anchor 152 is attached to a tension member 154, which may also be referred to as a tether. A push member 156 is also shown and is capable of advancement relative to the distal opening of the shaft 150. The tension member is kept under tension during insertion in order to retain the anchor 152 in the desired location relative to the push member 156 and shaft 150. A slider mechanism may be provided on a proximal portion the shaft 150, or at the junction 112 (FIG. 3) to keep the tension member 154 under appropriate tension until the anchor 152 is released as shown in FIG. 4B. Although the elements shown in FIG. 4A are illustrated in loose relationship to one another, this is merely for illustration. It should be understood that the anchor 152 and push member 156 in implementation would form a closer fit inside the lumen of the shaft 150. In an example, the push member 156 or shaft 150 may include a channel for the tension member 154 to reside in during use to avoid twisting or tangling during use.

Referring to FIG. 4B, once a layer of connective tissue 160 at the desired location is encountered, it is pierced using the anchor 152, preferably by pushing the push member 156 (FIG. 4A) distally. The push member 156 and shaft 150 (both FIG. 4A) are then withdrawn leaving the anchor 152 as shown, on one side of the connective tissue 160, with the tension member 154 crossing the connective tissue 160. Once so placed, the anchor is then available for anchoring a lead (shown below) in place after the lead is advanced over the tension member 156.

The tension member 154 may be as simple as a suture thread using, for example, any suitable natural or synthetic material. Though any material may be used for the tension member, it may be preferred to use prolene, which has minimal tissue reactiveness and will not resorb in the tissue; other materials such as catgut, nylon, polyglycolic acid or silk lose strength with time and may be less preferred. In part this is in recognition that the region the lead will be implanted in lacks significant vascularization and is less likely to have tissue ingrowth to hold a lead in place than happens, for example, with transvenous, intracardiac electrodes.

In an alternative embodiment, it may prove to be desirable to allow the tension member 154 to weaken or dissolve, to avoid undue tension on the connective tissue 160, for example, as the patient moves about. For such examples, the anchor 152 may be used primarily to achieve a desired implant location, while permanent anchoring of the lead into position can be achieved using, for example, a subcutaneously placed suture sleeve. For these alternatives, a resorbable or dissolving material, or a material that may weaken with time, may be used for the tension member 154, such as catgut, nylon, polyglycolic acid, or silk, or other materials.

Figure 5B:
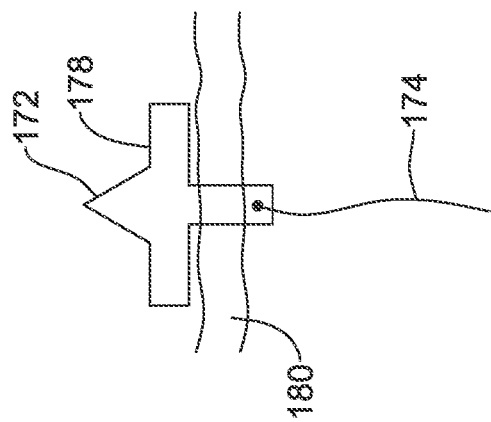
Figure 5A:
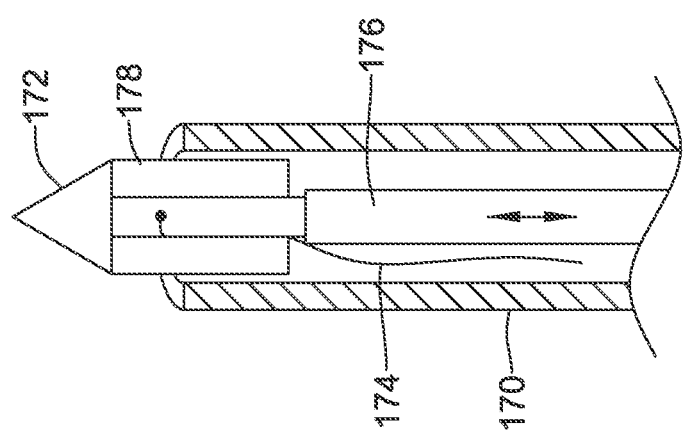

FIGS. 5A-5B show another example. Here, the shaft 170 has within it the anchor 172 attached to the tension member 174, with a push member 176 shown as well. The anchor 172 in this example has compressed arms 178 held in place with the distal tip of the shaft 170. As shown in FIG. 5B, actuation of the push member 176 pushes the distal tip of the anchor 172 into and through the target connective tissue 180 until the arms 178 extend outward beyond the connective tissue 180. The tension member 174 extends proximally therefrom, following retraction of the tube 170 and push member 176.

Figure 6:
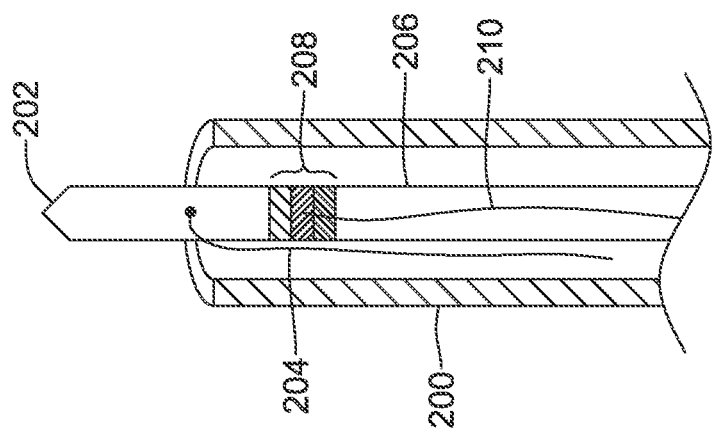

FIG. 6 shows an alternative using an ultrasonic localization tool. Here the shaft 200, anchor 202 and tension member 204 are largely as previously described relative to FIGS. 4A-4B. An ultrasonic transducer, such as a Doppler effect localization unit 208, is placed at the distal tip of the push member 206 with electrical connectors 210 extending therefrom. The Doppler effect localization unit is provided to aid the physician/implanter in identifying the position of the distal tip of the push member 206 in the patient during implantation, much as a Doppler needle would (see, for example, U.S. Pat. No. 4,887,606). Upon piercing through a tissue layer, the localization unit 208 output changes, allowing the physician to readily know when a desired location is accomplished.

The embodiment shown in FIG. 6 shows the pusher 206 having the Doppler localization unit. In one alternative example, the outer shaft 200 may take the form of a Doppler needle having a sharpened distal tip to use in piercing a desired connective tissue. For this example, during insertion the anchor 202 and push member 206 extend beyond the sharp distal tip until a desired connective tissue is encountered. The needle is then extended through the connective tissue using the Doppler unit to sense penetration. Once the connective tissue is penetrated, the anchor 202 can be advanced through the opening so made, and then twisted, turned, expanded or released to provide an anchor location.

In another example, during initial insertion a Doppler needle is contained inside shaft 200 until a desired connective tissue is reached. The Doppler needle can then be extended past the distal end of the shaft 200 to pierce the connective tissue, using the Doppler detection unit to determine when piercing is complete. An anchor is then pushed out the distal end of the Doppler needle to the desired location and twisted, turned, expanded or released.

In another example, an inner Doppler needle is used to pierce desired connective tissue after advancement within shaft 200, and the Doppler needle is removed and replaced with the combination anchor 202 and push member 206. The anchor is then advanced through the cut formed with the needle and twisted, turned, expanded or released. In another example, the outer shaft 200 may include an actuating cutting element to facilitate the creation of an opening through connective tissue, through which the anchor 202 and push member 206 can be advanced.

Figure 7B:
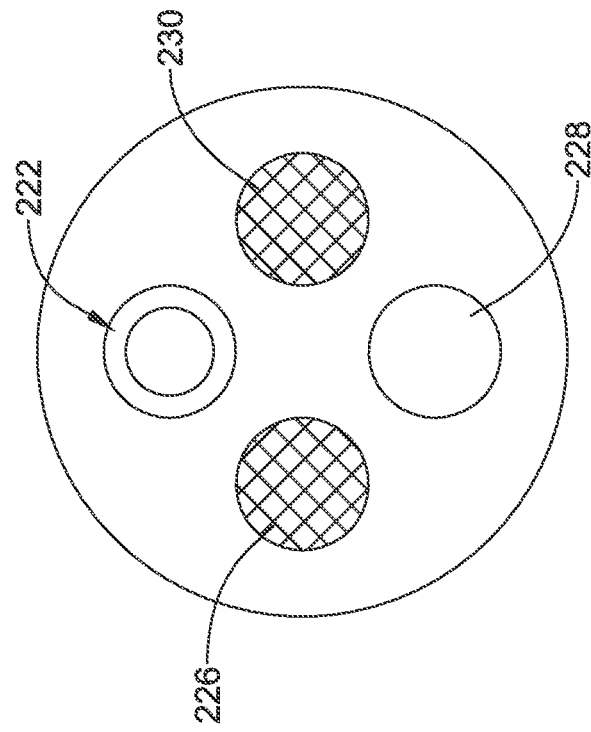
FIGS. 7A-7B illustrate another alternative for placement of an anchor.
Figure 7A:
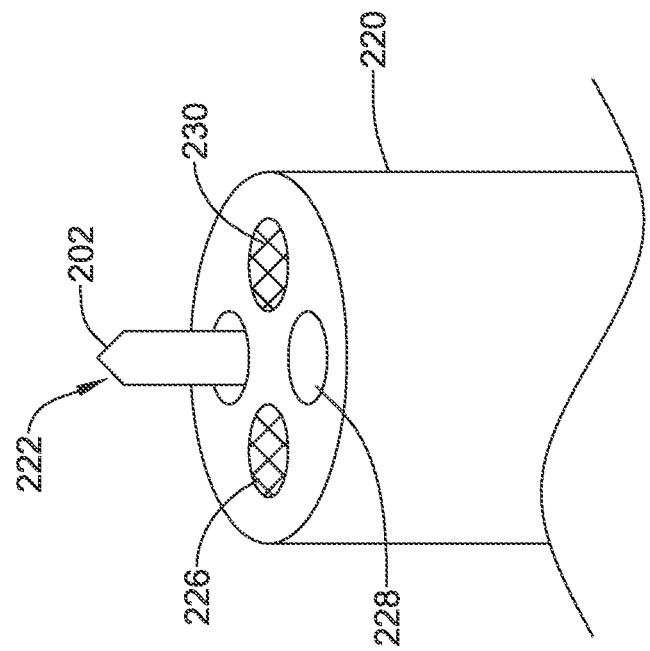

Another alternative is shown in FIGS. 7A-7B. Here an endoscopic unit is provided for implantation purposes. In this example, the endoscope 220 comprises a instrument channel 222 having within it an anchor, tension member and push member, and optionally an outer shaft as well, such as those shown in FIG. 4A or 5A. In addition, the endoscope 220 includes an illumination element 226, flush lumen 228, and visualization element 230. As is known for endoscopic arts, the illumination element is used to illuminate the vicinity of the distal tip, the visualization element 230 is used for observation of structures/objects or use of a tool in the instrument channel, for example, and the flush lumen may be used to inject air, saline or other material to clean off one or both lenses for the illumination/visualization elements, or to inject a therapeutic or other material, as needed. Some endoscopes and/or laparoscopes may include steering mechanisms as well. Thus this embodiment can be used to observe the anchoring procedure as it occurs to ensure that the anchor is placed as desired. FIG. 7B illustrates an end view of the endoscope 220 with the lenses for illumination element 226 and visualization element 230 shown as well as the flush lumen 228 and the instrument channel 222.

FIG. 8A shows an illustrative insertion sheath or tool. The sheath 300 includes an external port 302 and an insertion portion 304 having a curved shaft ending at an (optionally) beveled tip 306. The external port 302 may include one or more seals therein if desired. FIG. 8B shows a partial section view including some of the relevant anatomy including the sternum 312 including the manubrium 316, the xiphoid 318, and the sternal body 320, and the heart 314. As shown in the section view, when inserted, the insertion sheath may be sized and shaped to facilitate introduction around/beyond the xiphoid 318 while curving back in direction 310 toward the sternal body 320, away from the heart 314. The curvature of the insertion sheath biases an instrument passed through it toward the sternal body 320 and away from the heart 314 and pericardium. This length and curvature is not required, but may be advantageous in some examples.

Figure 9:
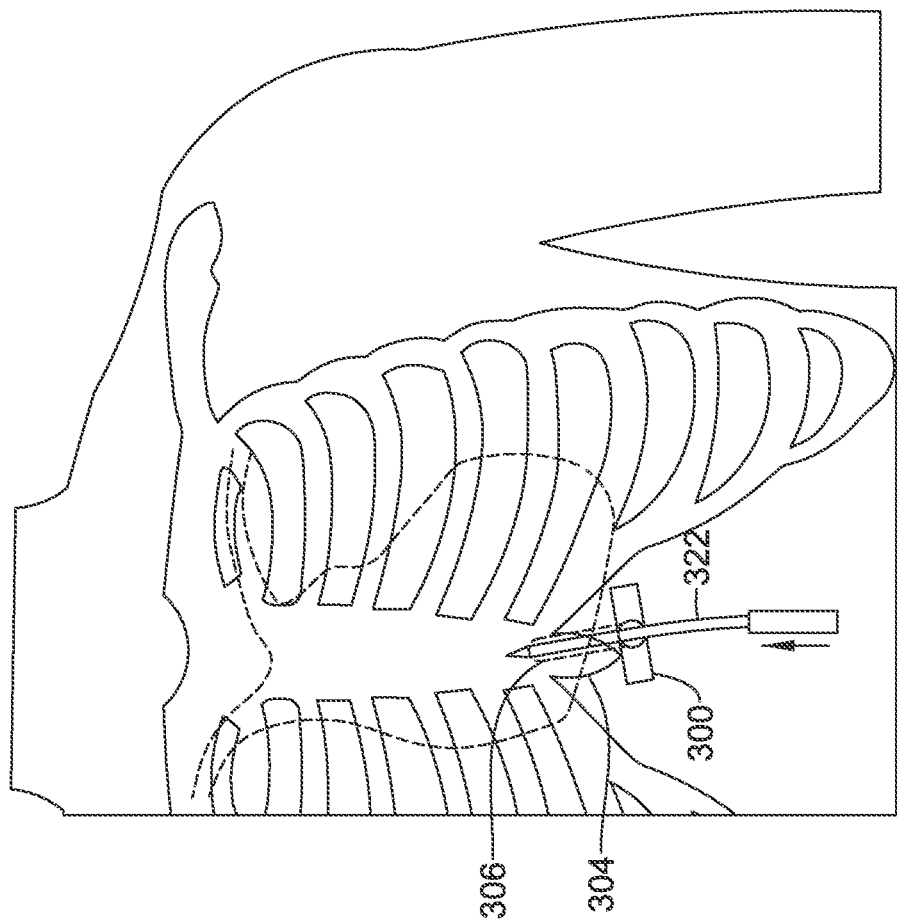
FIGS. 9-10 show frontal and side views of an illustrative implantation method.
Figure 10:
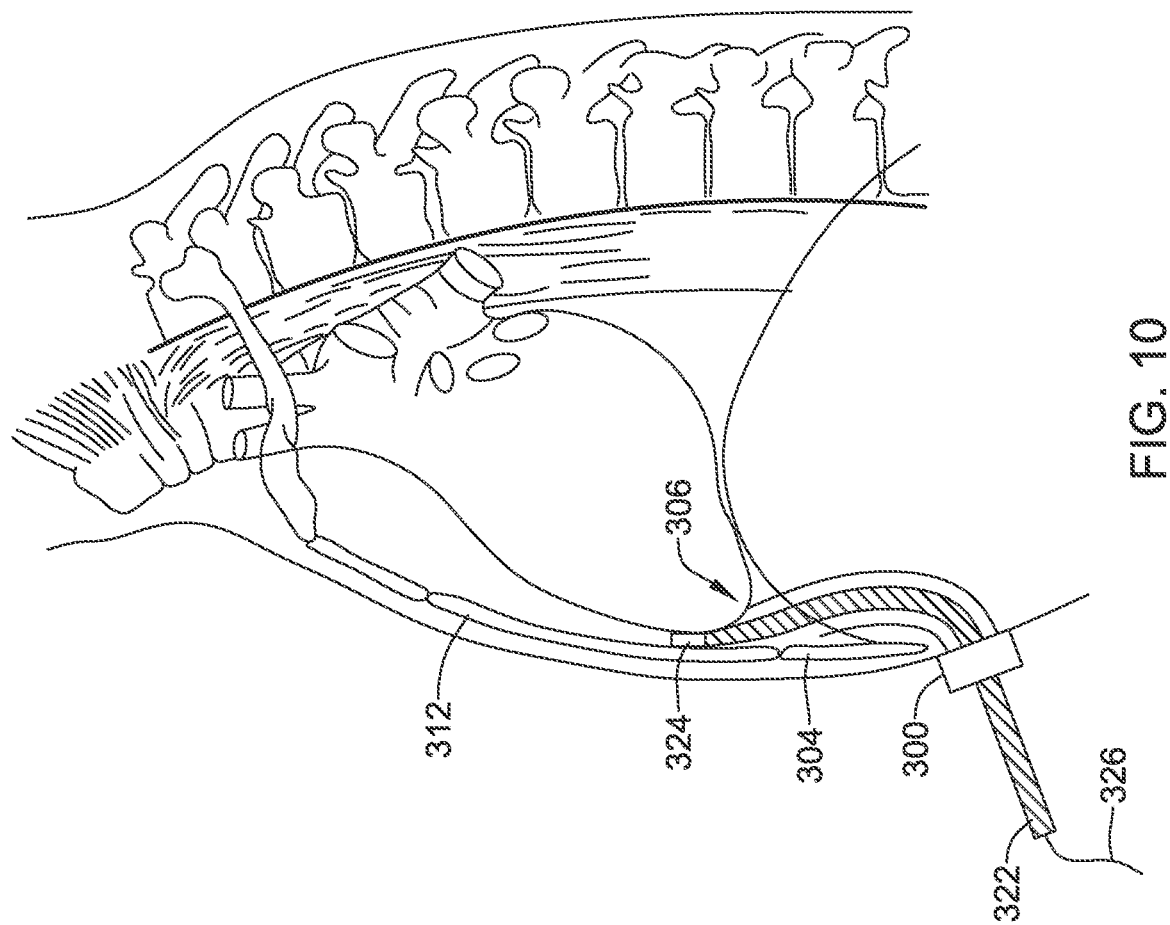

In use the insertion sheath 300 may be placed by the physician first making an incision inferior and/or lateral to the xiphoid and tunneling beneath the xiphoid using blunt dissection to allow ready placement of the insertion sheath 300 therethrough. Next, as shown in FIG. 9, the anchor placement tool 322 is advanced through the port of the insertion sheath 300 and exits the tip 306. As highlighted in FIG. 10, the curvature of the insertion sheath 300 biases the anchor placement tool 322 such that the distal end and anchor 324 is advanced along the back side of the sternal body 312.

Figure 11:
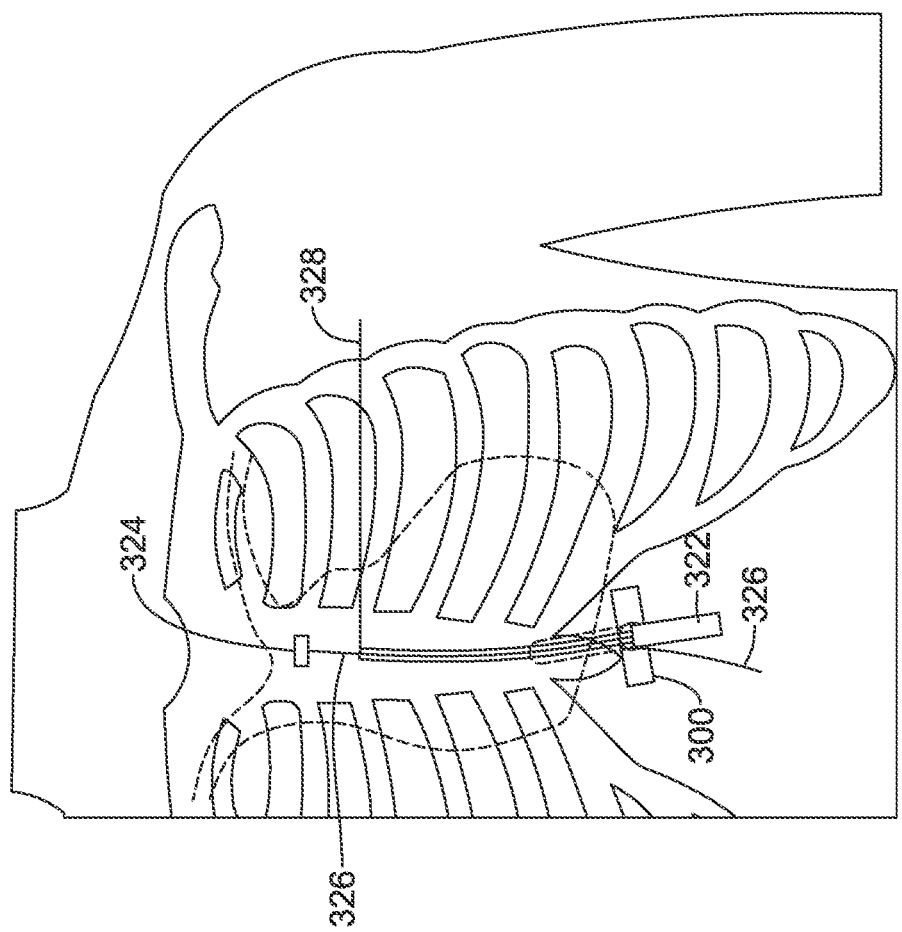
FIGS. 11-12 show frontal and side views of further steps in an illustrative implantation method.

FIG. 11 shows another frontal view with the anchor placement tool 322 fully inserted via the insertion sheath 300. The anchor 324 has been released past the desired connective tissue, just superior to the level of the sternal angle 328 in this example. Tension member 326 is attached to the anchor 324 and also exits the proximal end of the anchor placement tool 322. The tension member 326 may be provided with enough extra length to allow the entire anchor placement tool 322 to exit the insertion sheath 300 without releasing the proximal end of the tension member 326 in true over-the-wire fashion. If desired, instead, the anchor placement tool 322 may include a port at its distal end similar to a rapid-exchange port or single-operator exchange port, as is well known in the catheter arts, to allow the tension member 326 to exit near the distal end of the anchor placement tool 322.

Figure 12:
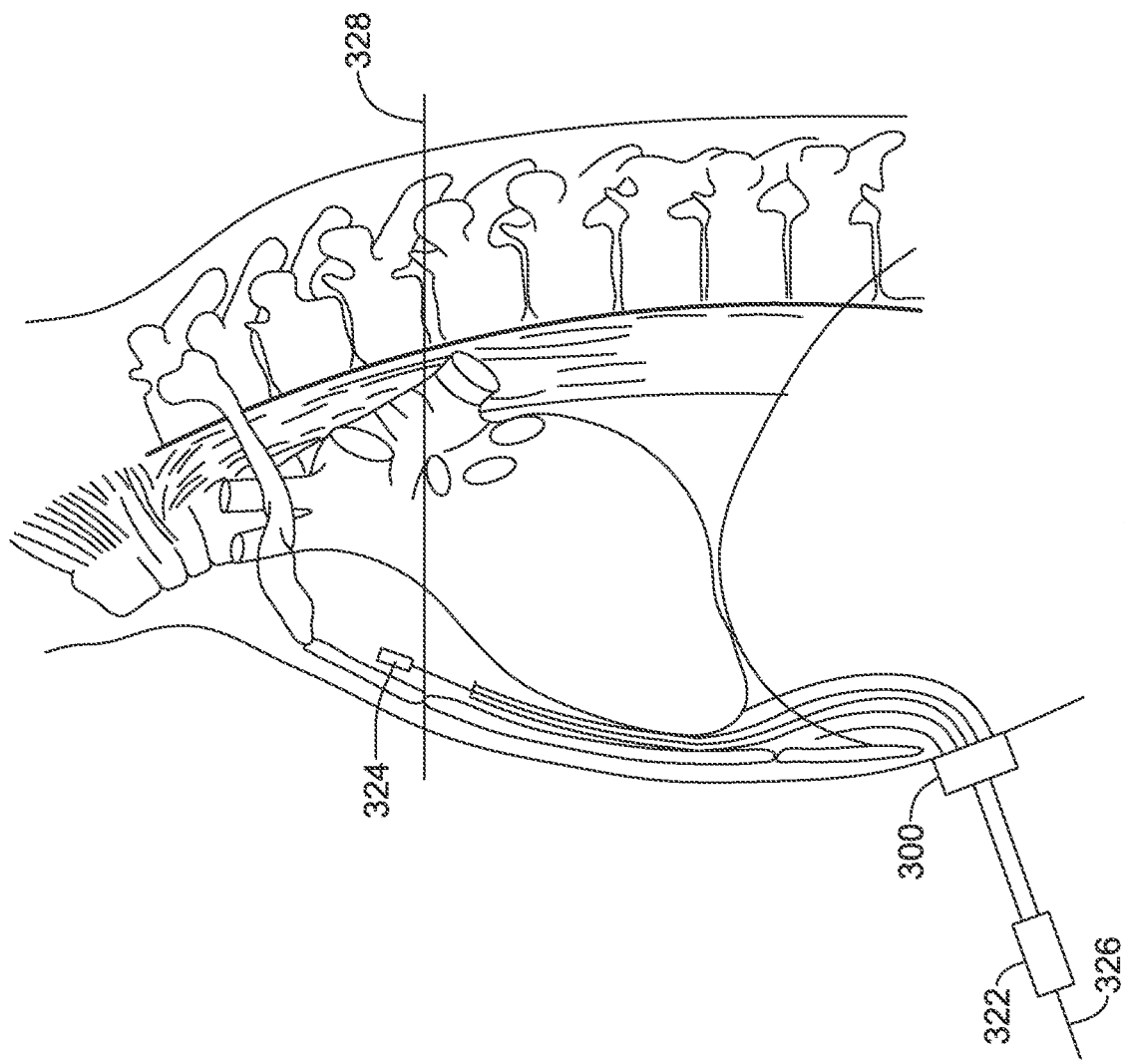

FIG. 12 corresponds to FIG. 11 but in side section view. The anchor tool 322 is shown generally fully inserted into the insertion sheath 300. The anchor 324 has been released superior to level of the sternal angle 328, approximately level with the aortic arch and superior to the ventricles of the heart; this location may also be approximately level with the thymus (not shown). Though shown separately for illustration, at this stage of implantation the proximal handle of the anchor placement tool 322 may be adjacent the external portion of the insertion sheath 300, with the tension member 326 accessible as shown at the proximal end.

Figure 13:
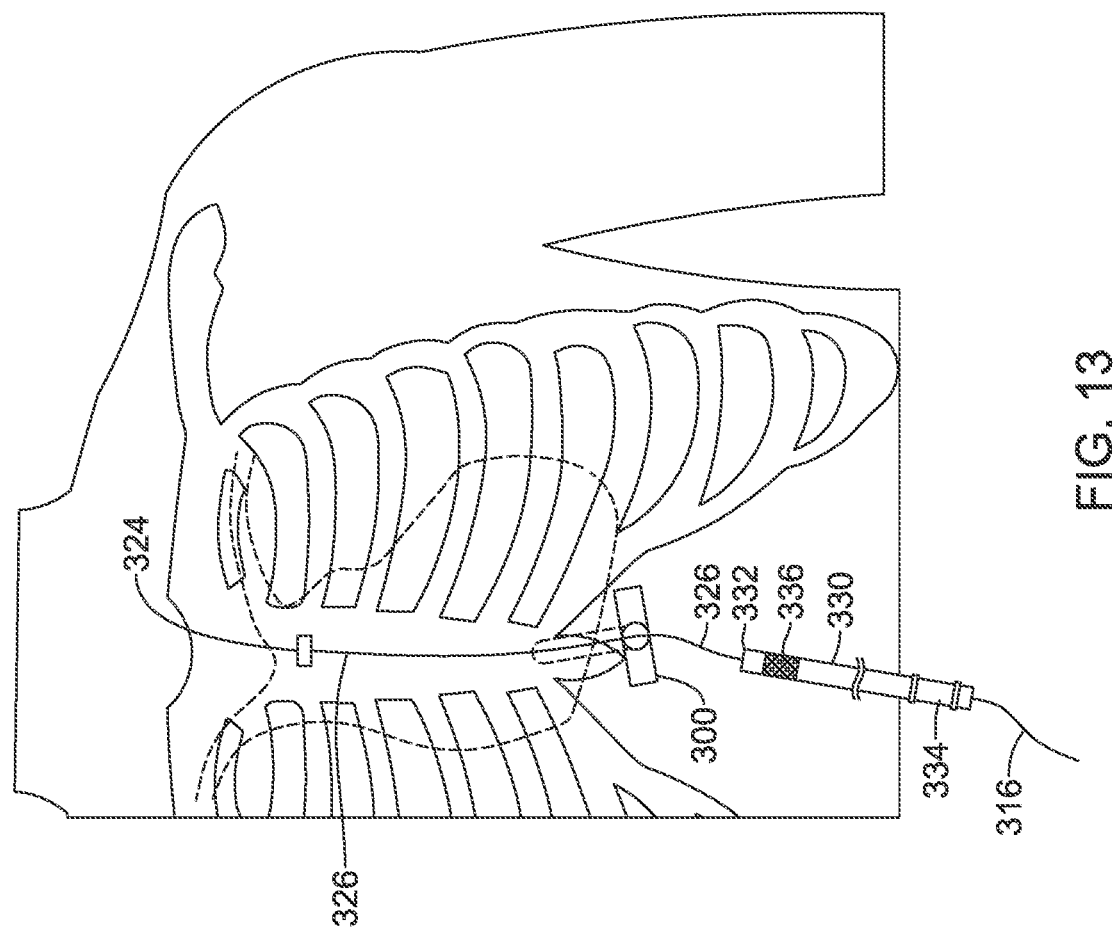
FIG. 13 shows a frontal view of a next step after an anchor is placed in an illustrative implantation method.

Following the release of the anchor 324 as shown in FIG. 11, the anchor placement tool 322 can be withdrawn via the insertion sheath 300. As shown in FIG. 13, this leaves the anchor 324 at a desired location. The desired location may be, for example, adjacent the posterior of the sternum in the thoracic cavity of a patient, which facilitates securing the distal portion of a cardiac sensing and/or therapy lead at or near the anchor in a location between the ribcage and heart of the patient, without attachment to the heart or pericardium. Such placement at the desired location, as shown in the preceding figures, is performed by inserting a stylet or cannula beneath the sternum from a location near the patient's xiphoid and advancing a distal portion of the stylet or cannula to a desired location for the anchor. The desired location may correspond to one or more of a location approximately at the sternal angle, a location between the second and third ribs; a location approximately level with the thymus; a location level with the aortic arch; and a location level with the superior vena cava. A given implant position may meet the descriptions of a plurality of these illustrative locations. During placement of the anchor, fluoroscopic or other visualization may be used to achieve a desired position, though this is not necessary.

In FIG. 13, the tension member 326 passes through the insertion sheath 300 and out of the patient, preferably through a seal in the insertion sheath 300, with such seal having any suitable form known in the art, for example, of laparoscopic devices. A lead 330 having a distal tip 332, a proximal end 334, and one or more electrodes 336 thereon, is shown threaded over the tension member 326. Though FIG. 13 shows an "over the wire" relationship between lead 330 and tension member 326, if desired, a port may be placed anywhere distal of the proximal end 334 (including near the electrode 336, nearer the distal 332 than the proximal end 334, or just distal of the seal plug shown at the proximal end 334) to allow exit of the tension member without passing through the entire length of the lead 330.

Figure 14A:
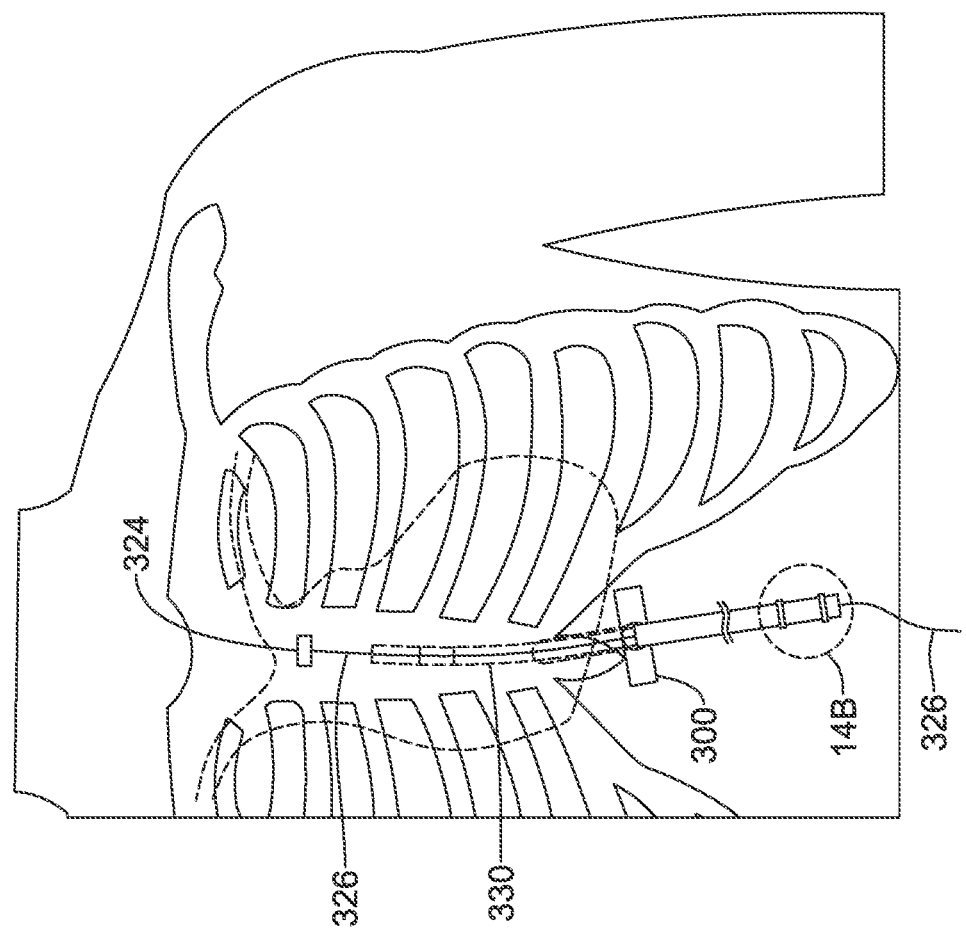
FIG. 14A shows a frontal view of a next step following the step shown by FIG. 13.
Figure 14B:
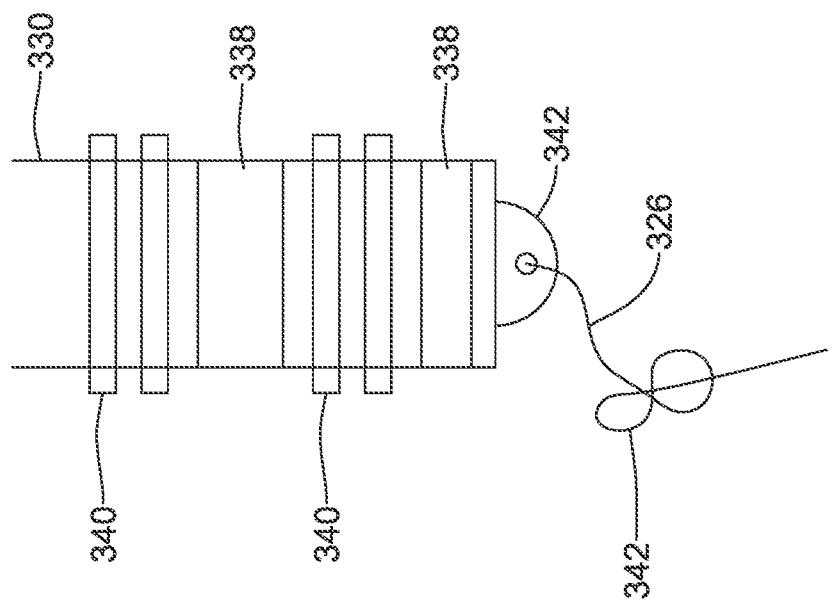
FIG. 14B provides a detail view at the proximal end of the lead in FIG. 14A.

As shown in FIG. 14A, the lead 330 is then passed over the tension member until a desired position is achieved relative to the anchor 324. The tension member 326 may be used to secure the lead 330 relative to the anchor 324 by tying the tension member 326 to the proximal end of the lead 330. FIG. 14B shows the tying step in detail, with the lead 330 having contacts 338 and seals 340 and, at its very proximal end, a tying structure 342 shown as a suture hole. The tension member 326 may be tied to the tying structure 342 or may be knotted onto itself as shown at 342 to prevent movement of the proximal end of the lead 330 proximally. In this example it can be noted that the tension member 326 would be held with slight tension/pressure while the lead is advanced toward the anchor. During lead insertion, fluoroscopic or other visualization may be used to achieve a desired position, though this is not necessary.

In another example, a port may be provided on the lead 330 at a location spaced from the distal tip so as to be near the xiphoid of the patient. A suture sleeve may be provided near the xiphoid, for example, with the tension member tied to the suture sleeve. The tension member 326 itself, or, alternatively, a separate suture, may be used subcutaneously anchor the lead 330 in place at a location near the xiphoid or along a path leading toward and/or at the canister (see FIGS. 15-16, below) using the suture sleeve, if desired.

Figure 16:
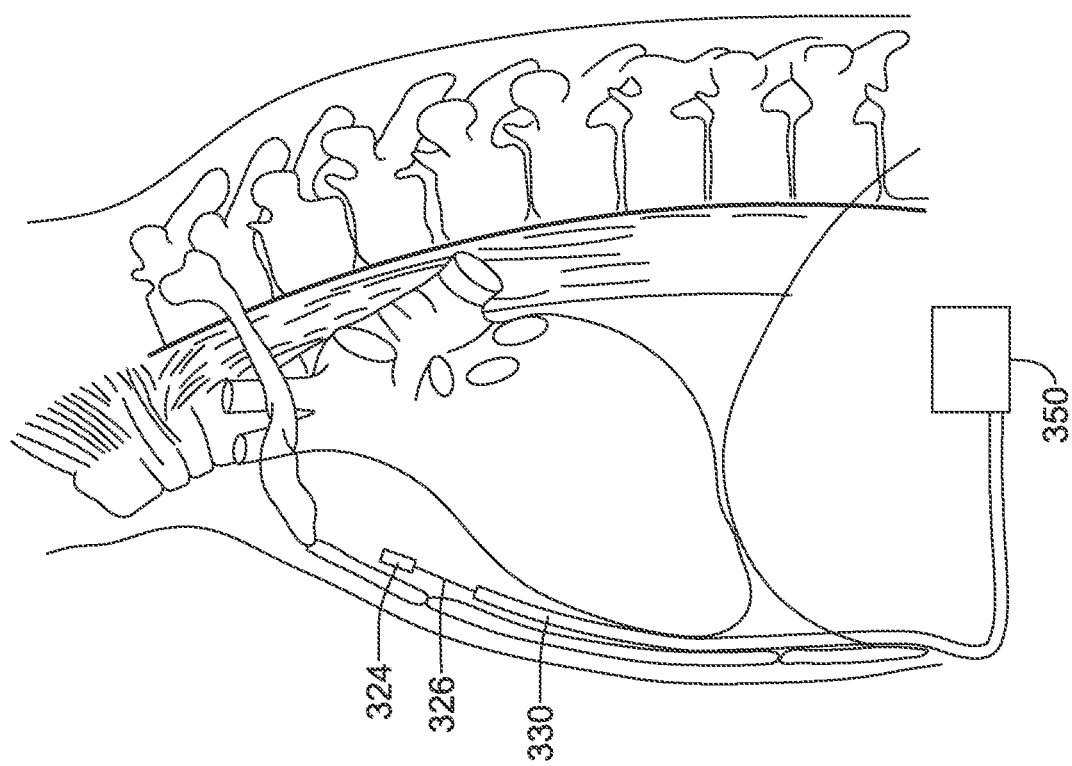

FIGS. 15-16 show frontal and side views of an implanted configuration following completion of an illustrative method. Here, the anchor 324 remains connected to the tension member 326, which enters the lead 330 within the thorax, beneath the ribcage but outside of the pericardium. The proximal end of the lead 330 has been tunneled to a canister 350. The canister 350 houses the operational circuitry of the system, including therapy output circuitry, controller circuitry, and a power source such as a battery, for example. The side view of FIG. 16 illustrates how the lead 330 is placed anterior to the heart and pericardium, with the anchor 324 superior to the ventricles. The lead 330 is routed over the tension member 326.

In the example of FIGS. 15-16, a canister 350 has been placed subcutaneously over the ribs of the patient at the left axilla, generally at or anterior to the left mid-axillary line. More anterior or posterior positions may be used instead. The canister is shown placed approximately level with the cardiac apex, or in line with the ventricles, though a higher or lower position may be used instead.

In still further options, the canister may be placed at a pectoral location, level with the atria or even superior to the heart. If the canister 350 is placed in a high pectoral position such as near the clavicle, the lead 330 may be tunneled from a superior location near or above the manubrium and down toward the xiphoid, if desired. It is, however, expected that the implant procedure illustrated above, with access near the xiphoid, may be easier for the physician.

The canister 350 will typically be a hermetically sealed unit that houses operational circuitry for the implantable system. The operational circuitry may include various elements such as a battery, and one or more of low-power and high-power circuitry. Low-power circuitry may be used for sensing cardiac signals including filtering, amplifying and digitizing sensed data. Low-power circuitry may also be used for certain cardiac therapy outputs such as pacing output, as well as an annunciator, such as a beeper or buzzer, telemetry circuitry for RF, conducted or inductive communication (or, alternatively, infrared, sonic and/or cellular) for use with a non-implanted programmer or communicator. Memory and logic circuitry will also be provided, typically. Such elements typically couple with one another via a control module which may include a controller or processor. High power circuitry such as high power capacitors, a charger, and an output circuit such as an H-bridge having high power switches may also be provided for delivering, for example, defibrillation therapy. Other circuitry and actuators may be included such as an accelerometer or thermistor to detected changes in patient position or temperature for various purposes, output actuators for delivering a therapeutic substance such as a drug or insulin replacement, for example.

Some additional examples for hardware, leads and the like for implantable defibrillators may be found in commercially available systems such as the Boston Scientific Teligen™ ICD and S-ICD™ System, Medtronic Concerto™ and Virtuoso™ systems, and St. Jude Medical Promote™ RF and Current™ RF systems, as well as the leads provided for use with such systems.

These various elements are not all required in any one system. For example, a device may use conducted emissions for communication, provided through the input/output circuitry and omit a telemetry circuit entirely. A lower power stimulus device (such as a pacemaker or CRT-P device) may omit the high power circuit. A rechargeable device may include a recharge circuit coupled to the power supply and replenishable battery. Output circuits and high power circuitry may be left out of an implantable loop recorder.

Figure 17:
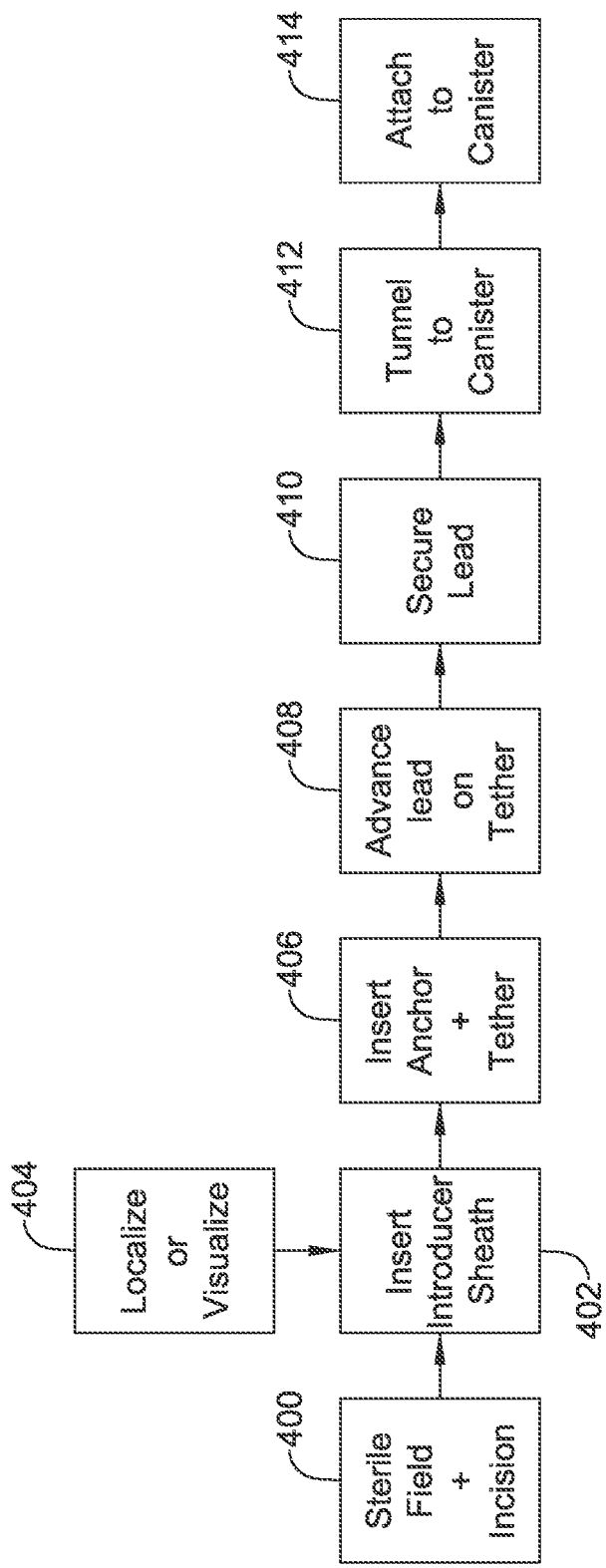
FIGS. 17-18 are block flow diagrams for illustrative methods.
Figure 18:
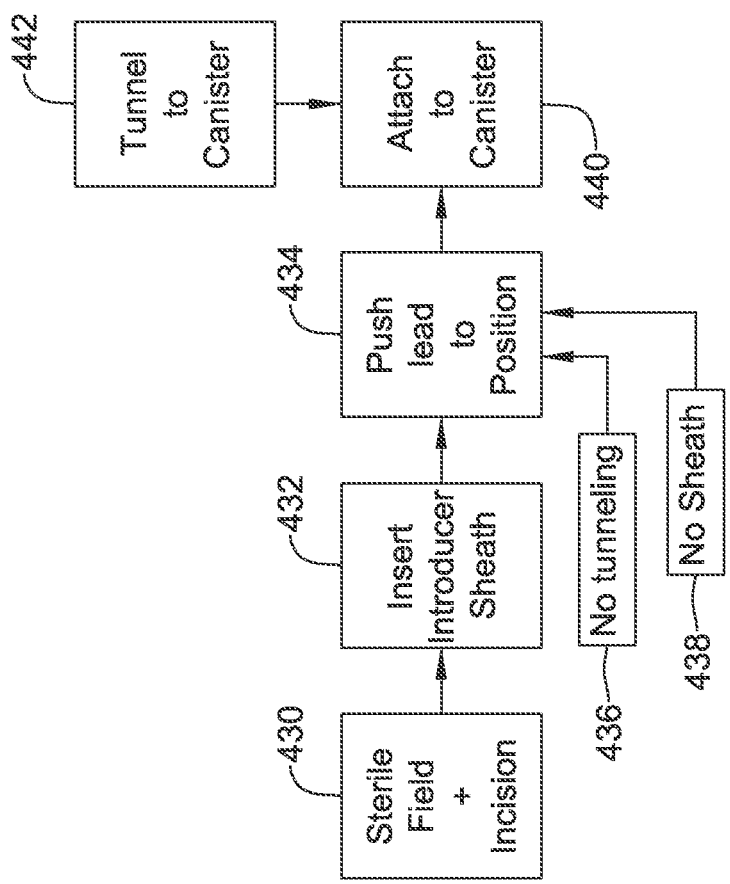

FIGS. 17-18 are block flow diagrams for illustrative methods. In the illustrative method of FIG. 17, an implant procedure begins by preparing the sterile field and making an incision, as shown at 400. An introducer sheath or insertion sheath (these two terms are interchangeable for purposes herein) is then inserted via the incision, as shown at 402; visualization may be used as indicated at 404. For example, the incision may be near the xiphoid, and the insertion of the introducer sheath can access beneath the xiphoid to the back side of the sternum. Preferably the introducer sheath does not enter or damage any of the diaphragm, pericardium or lungs during the insertion 402. In some examples, a guidewire may be first introduced to a desired position with the insertion sheath (possibly including a dilator inserted therethrough with a cone-shaped distal end) passed thereover; the guidewire and dilator, if any, can then be removed. Next the anchor insertion tool and associated tether or tension member is inserted, as shown at 406. The anchor is placed in a desired location and anchored to tissue during step 406, and the insertion tool is removed, leaving the anchor in place with the tether/tension member left in place.

Next, the lead is advanced over the tether/tension member, as shown at 408. Notably, in some examples, neither "tunneling", nor a sheath (other than the introducer sheath) is used during the step at 408. Next, the lead once placed may be secured using the tether/tension member, as indicated at 410. Thus, in block 410, the lead would be secured relative to the anchor that was placed in step 406. Then, if needed, the proximal end of the lead can be subcutaneously tunneled to the canister, as shown at 412, and then attached to the canister 414.

FIG. 18 illustrates another method, again beginning with preparation of the sterile field and placement of an incision at 430, followed by insertion of the introducer or insertion sheath 432. The lead is then pushed into position, as shown at 434. In one example, the lead may be pushed into position by inserting a stylet in the lead and advancing a distal tip of the lead to a desired placement. In another example, as shown above in FIGS. 9-16, a tether or tension member is used in association with an anchor to establish a track over which the lead may be placed. In either example, a lead is placed beneath the ribs and/or sternum without tunneling in the mediastinum as noted at 436, and a sheath is not used as shown at 438.

By the reference to not using a sheath at 438, it is intended that an introducer sheath may be used to achieve an initial starting place for insertion, but a sheath as shown in the Guenther et al. article may be omitted. In the Guenther et al. article, the sheath was placed over an insertion tool for tunneling and left in place while the insertion tool is removed, thus maintaining an avenue for insertion of the lead within the sheath. As an alternative, one may describe the insertion shown above as being an over-the wire insertion where the lead is inserted over a tether/tension member which is inserted into the lead at the distal end of the lead. An over-the-wire insertion would have the tether/tension member disposed within the lead for all or nearly all of its length; as an alternative, a single-operator-exchange or rapid exchange configuration would have the tether/tension member exit the interior of the lead at some location distal of the proximal end of the lead.

Once the lead is pushed into position, as shown at 434, it can be attached to a canister for the system as shown at 440. In some examples there is also a separate step of tunneling to the canister, as indicated at 442.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description.

The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A method of placing a lead at a desired location for an implantable cardiac therapy system, the lead having a proximal end and a distal end, the distal end including one or more electrodes, the method comprising:

advancing an insertion sheath having a proximal end and a distal end percutaneously near the xiphoid of the patient to position the distal end of the insertion sheath along the back side of the sternum superior to the xiphoid, wherein the insertion sheath is shaped to direct a member passed therethrough against the back of the sternum; and advancing the lead through the insertion sheath until the distal end of the lead is at the desired location, wherein the desired location is along the posterior of the sternum.

2. The method of claim 1 wherein the step of advancing the insertion sheath percutaneously is performed without first tunneling any instrument to the desired location.

3. The method of claim 1 wherein the distal end of the insertion sheath is configured to avoid directing the lead into contact with cardiac tissue of the patient.

4. The method of claim 3 wherein the cardiac tissue includes the pericardium.

5. The method of claim 1 further comprising:
making an incision inferior and/or lateral to the xiphoid; and
bluntly dissecting tissue before advancing the insertion sheath.

6. The method of claim 1 wherein the desired location is superior to the ventricles of the patient's heart.

7. The method of claim 1 wherein the desired location is one of:
a location at or superior to the sternal angle;
a location between the second and third ribs;
a location level with the thymus;
a location even with the aortic arch; and
a location even with the stop of the superior vena cava.

8. The method of claim 1 further comprising:
implanting a canister at the patient's left axilla;
subcutaneously tunneling a proximal end of the lead to the left axilla; and
coupling the proximal end of the lead to the canister; wherein the canister houses defibrillation circuitry.

9. The method of claim 1 further comprising:
passing an anchor and an anchor placement tool through the insertion sheath;
releasing the anchor from the anchor placement tool, wherein the anchor is connected to a tension member which passes through the anchor placement tool; and
removing the anchor placement tool.

10. The method of claim 9, wherein the step of advancing the lead comprises passing the lead over the tension member.

11. The method of claim 1, wherein advancing the lead includes inserting a stylet in the lead and using the stylet to push the lead to the desired location.

12. The method of claim 1, wherein the insertion sheath includes an insertion portion having a curved shaft and a tip, wherein advancing the insertion sheath includes inserting the insertion sheath adjacent a patient's xiphoid and curving the insertion portion around the xiphoid in a direction toward the patient's sternal body.

13. The method of claim 12, wherein curving the insertion portion around the xiphoid includes moving the insertion portion away from the patient's heart and pericardium and along a back side of the patient's sternal body.

14. The method of claim 1 wherein the step of advancing the insertion sheath comprises advancing the insertion sheath with a dilator inserted therethrough.

15. The method of claim 14 wherein the step of advancing the insertion sheath with the dilator inserted therethrough comprises passing the dilator over a guidewire.

\* \* \* \* \*